United States Patent [19]

Nicolau et al.

[11] Patent Number: 5,731,457
[45] Date of Patent: Mar. 24, 1998

[54] VINYL ACETATE PROCESS UTILIZING A PALLADIUM-GOLD-COPPER CATALYST

[75] Inventors: Ioan Nicolau; Jerry A. Broussard; Philip M. Colling, all of Corpus Christi, Tex.

[73] Assignee: Hoechst Celanese Corporation, Warren, N.J.

[21] Appl. No.: 870,120

[22] Filed: Jun. 3, 1997

[51] Int. Cl.$^6$ .................................................. C07C 67/05
[52] U.S. Cl. .................................................... 560/245
[58] Field of Search .................................... 560/245

[56] References Cited

U.S. PATENT DOCUMENTS

| | | | |
|---|---|---|---|
| 3,625,998 | 12/1971 | Fernholz | 560/245 |
| 3,670,014 | 6/1972 | Fernholz | 560/245 |
| 5,185,308 | 2/1993 | Bartley et al. | 502/170 |
| 5,274,181 | 12/1993 | Bartley et al. | 560/245 |
| 5,292,931 | 3/1994 | Wirtz | 560/245 |
| 5,332,710 | 7/1994 | Nicolau et al. | 502/243 |
| 5,347,046 | 9/1994 | White et al. | 560/245 |
| 5,422,329 | 6/1995 | Wirtz et al. | 502/328 |
| 5,550,281 | 8/1996 | Cirjak | 560/245 |

*Primary Examiner*—Michael L. Shippen
*Attorney, Agent, or Firm*—M. Susan Spiering

[57] ABSTRACT

A process is disclosed for the production of vinyl acetate by reaction of ethylene, oxygen and acetic acid as reactants comprising contacting said reactants and a non-halogen containing copper compound with a catalyst comprising a porous support on the porous surfaces of which is deposited catalytically effective amounts of metallic palladium, gold and copper. During the process to prepare vinyl acetate, a stream of alkali metal acetate is preferably passed over the catalyst. The process results in higher vinyl acetate selectivity and productivity due to lower $CO_2$ selectivity during the life of the catalyst, and/or longer catalyst life.

19 Claims, No Drawings

VINYL ACETATE PROCESS UTILIZING A PALLADIUM-GOLD-COPPER CATALYST

BACKGROUND OF THE INVENTION

1. Field of the Invention

This invention relates to a new and improved process for the production of vinyl acetate ("VA") by reaction of ethylene, oxygen and acetic acid. Particularly, this invention relates to the use of non-halogen containing copper compound during the production of VA.

2. Background Information Including Description of Related Art

It is known to produce vinyl acetate by reaction of ethylene, oxygen and acetic acid using a catalyst consisting of palladium, gold and copper supported on a carrier. While the process utilizing such a catalyst is capable of producing vinyl acetate at relatively high levels of productivity, any expedient resulting in even greater productivity over the life of the catalyst would be very desirable.

The following references may be considered material to the invention claimed herein.

U.S. Pat. No. 5,332,710, issued Jul. 26, 1994 to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution to precipitate such compounds, and subsequently reducing the compounds to free metallic form.

U.S. Pat. No. 5,347,046, issued Sep. 13, 1994 to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

SUMMARY OF THE INVENTION

In accordance with this invention, a process is provided for the production of vinyl acetate by reaction of ethylene, oxygen and acetic acid with low carbon dioxide selectivity, utilizing a catalyst comprising a porous support on the porous surfaces of which is deposited catalytically effective amounts of metallic palladium, gold, and copper, wherein a non-halogen containing copper compound is included in the feed of reactants to the process. By means of this process, the amount of copper lost by the catalyst volatilization during long term use is replaced, resulting in less of a rise in carbon dioxide selectivity, and therefore less of a loss of vinyl acetate productivity due to such use, than when no copper compound is included in the feed.

DETAILED DESCRIPTION OF THE INVENTION

Related to the invention claimed herein is the discovery, not appreciated heretofore, that during the production of vinyl acetate using a supported palladium-gold-copper catalyst, the copper content of the catalyst tends to be substantially reduced during the life of the catalyst, i.e., before it is necessary to replace or regenerate the catalyst, which may approach or exceed two years. Such loss of copper is apparently due to the fact that under reaction conditions, the copper which is at or near the surface of the catalyst particles, reacts with one or more of the reactants to form a compound with a tendency to sublime. In the process of the invention, however, a significant amount or all of the copper initially deposited on the support surfaces of the catalyst, which would ordinarily be lost during the life of the catalyst, is replaced by the copper in the feed. This causes less of a reduction in the amount of copper in the catalyst due to sublimation than when no copper compound is included in the feed. In this connection, it is noted that while the carbon dioxide selectivity of a vinyl acetate process utilizing any supported palladium-gold catalyst tends to rise during the life of the catalyst, i.e., from the time fresh catalyst is charged to the reactor to the time the reactor is shut down for the purpose of replacing or regenerating the catalyst, such carbon dioxide selectivity is generally lower during any point in the life of the catalyst when the catalyst contains a certain amount of copper in addition to palladium and gold than when no copper or less copper is present. Thus, the loss of a smaller amount of copper during the life of a catalyst under this invention results in higher overall vinyl acetate productivity than when employing a platinum-gold-copper catalyst in which no copper compound is included in the feed.

The catalyst support material is composed of particles having any of various regular or irregular shapes, such as spheres, tablets, cylinders, rings, stars, or other shapes, mad may have dimensions such as diameter length or width of about 1 to about 10 mm, preferably about 3 to 9 mm. Spheres having a diameter of about 4 to about 8 mm are preferred. The support material may be composed of any suitable porous substance, e.g., silica, alumina, silica-alumina, titania, zirconia, silicates, aluminosilicates, titanates, spinel, silicon carbide, or carbon and the like.

The support material may have a surface area within the range, for example, of about 10 to about 350 $m^2/g$, preferably about 100 to about 200 $m^2/g$, an average pore size in the range, for example, of about 50 to about 2000 angstroms, and a pore volume in the range, for example, of about 0.1 to 2, preferably about 0.4 to about 1.2 ml/g.

In the preparation of the catalyst used in the process of this invention, the support material is treated to deposit catalytic amounts of palladium, gold and copper on the porous surfaces of the support particles. Any of various methods for accomplishing this purpose may be used, all of which involve simultaneous or separate impregnations of the support with one or more aqueous solutions of water-soluble compounds of copper, palladium and/or gold. Palladium (II) chloride, sodium palladium (II) chloride, potassium palladium (II) chloride, palladium (II) nitrate or palladium (II) sulfate are examples of suitable water-soluble palladium compounds, while an alkali metal, e.g., sodium or potassium salt of auric (III) chloride or tetrachloroauric (III) acid can be used as the water-soluble gold compound, and cupric nitrate trihydrate or hexahydrate, cupric chloride (anhydrous or dihydrate), cupric acetate monohydrate, cupric sulfate (anhydrous or pentahydrate), cupric bromide or cupric formate (anhydrous or tetrahydrate), can be used as the water-soluble copper compound. An alkali metal salt of tetrachloroauric (III) acid, sodium palladium (II) chloride and cupric nitrate trihydrate or cupric chloride are preferred salts for impregnation because of their good water solubility.

As mentioned above, any method known to those of skill in the art may be employed for the impregnation of palladium, gold or copper onto the support. Preferably, the impregnation is accomplished by the "incipient wetness" method wherein an amount of water-soluble metal compound solution used for the impregnation is from about 95 to about 100 percent of the absorptive capacity of the support material. The concentration of the solution or solutions is such that the amount of elemental palladium, gold and copper in the solution or solutions absorbed on the support is equal to a desired predetermined amount. If more than one such impregnation is carried out, then each impregnation may contain water-soluble compound equivalent to all or only a portion of the amount of one or any combination of the three catalytically active metals desired in the final catalyst, as long as the amounts of such metals in the total of the impregnating solutions absorbed are equal to the final desired amounts. In particular, it may be desirable to impregnate the support with more than one solution of a water-soluble gold compound, as more fully described hereinafter. The impregnations are such as to provide, for example, about 1 to about 10 grams of elemental palladium; for example, about 0.5 to about 10 grams of elemental gold; and, for example, about 0.3 to about 5.0 grams, preferably about 0.5 to about 3.0 grams, of elemental copper per liter of finished catalyst, with the amount of gold being from about 10 to about 125 weight percent based on the weight of palladium.

After each impregnation of the support with an aqueous solution of water-soluble salt of a catalytically active metal, the metal is "fixed", i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkali metal in the alkaline compound should be in an amount of, for example, about 1 to about 2, preferably about 1.1 to about 1.6 moles per mole of anion present in the water-soluble salt. The fixing of the metal may be done by the incipient wetness method wherein the impregnated support is dried, e.g., at a temperature of 150° C. for one hour, contacted with an amount of solution of the alkaline material equal to about 95–100% of the pore volume of the support, and allowed to stand for a period of about ½ hour to about 16 hours; or the roto-immersion method wherein the impregnated support without drying is immersed in a solution of the alkaline material and is rotated and/or tumbled during at least the initial period of precipitation such that a thin band of the precipitated water-insoluble compound is formed at or near the surface of the support particles. The rotation and tumbling may be carried out, for example, at about 1 to about 10 rpm for a period of about 0.5 to about 4 hours. The contemplated roto-immersion method is disclosed in U.S. Pat. No. 5,332,710, the entire disclosure of which is incorporated herein by reference.

The fixed, i.e., precipitated palladium, gold and copper compounds may then be reduced, for example, in the vapor phase with ethylene, e.g., 5% in nitrogen at 150° C. for about 5 hours after first washing the catalyst containing the fixed metal compounds, until it is free of anions such as halide, and drying, e.g., at 150° C. for about 1 hour, or such reduction may be accomplished before washing and drying in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed metal compounds present on the support may be employed as known in the art. The reduction of the fixed metal compound mainly results in the formation of the free metal, although a minor amount of metal oxide may also be present. In preparations using more than one impregnation and fixing steps, the reduction may be carried out after each fixing step or after the total of the metallic elements have been fixed on the support.

As an example of foregoing general procedure, a "separate fix" method may be used to fix the catalytically active metallic elements on the support and reduce the water-insoluble metal compounds to the desirable free metallic form. In this method, using the specific procedures described previously, the support is first impregnated with an aqueous solution of water-soluble compounds of palladium and copper by incipient wetness, and the palladium and copper are then fixed by treatment with an alkaline fixing solution by conventional techniques such as incipient wetness or roto-immersion, preferably roto-immersion. The catalyst is then dried and separately impregnated with a solution of a soluble gold compound having the amount of elemental gold desired in the catalyst, and the gold is fixed by treatment with an alkaline fixing solution by incipient wetness or roto-immersion, preferably incipient wetness. If the gold is to be fixed by the incipient wetness method, such fixing may be combined with the impregnation step by using a single aqueous solution of soluble gold compound and alkaline fixing compound in an amount in excess of that necessary to convert all the gold in the solution to a fixed insoluble gold compound, e.g., auric hydroxide. If a hydrocarbon such as ethylene, or hydrogen is to be used in the vapor phase as reducing agent, the catalyst containing the fixed metal compounds is washed until it is free of anions, dried, and reduced with ethylene or other hydrocarbon as previously described. If hydrazine is to be used in the liquid phase as reducing agent, the catalyst containing the fixed metal compounds is treated with an aqueous solution of excess hydrazine hydrate before washing and drying to reduce the metal compounds to the free metals, and the catalyst is then washed and dried as described.

Another alternate method of preparing the catalyst is a "modified roto-immersion" method in which only part of the gold is impregnated with the palladium and copper in a first impregnation, the metals are fixed by reaction with an alkaline fixing compound by roto-immersion, the fixed metal compounds are reduced to the free metals, e.g., with ethylene or hydrazine hydrate, with washing and drying done before an ethylene reduction or after a hydrazine reduction. The catalyst is then impregnated with the remainder of the gold in the form of a solution of water soluble gold compound, and the catalyst is again reduced, e.g., with ethylene or hydrazine, after or before washing and drying, as described previously.

An advantageous variant of a catalyst which may be used in the process of this invention comprises a porous support on the porous surfaces of which is deposited metallic copper in a zone surrounded by deposits of catalytically effective amounts of metallic palladium and gold, neither of which is substantially intermingled with said copper. This catalyst may be prepared using various techniques of impregnation, fixing and reduction as described hereinbefore. The use of this catalyst in which the zone of copper is surrounded by the palladium and gold and the copper is therefore less exposed to ambient reactor conditions, contributes to a reduction in the loss of copper and thus to a decrease in the fall of vinyl acetate productivity, during the life of the catalyst.

After the catalyst containing palladium, gold, and copper in free metallic form deposited on a support material is prepared by any of the foregoing methods, it is advantageously further impregnated with a solution of an alkali metal acetate, preferably potassium or sodium acetate, and most preferably potassium acetate. The catalyst is then dried such that the finished catalyst contains, for example, about 10 to about 70 grams, preferably about 20 to about 60 grams of alkali metal acetate per liter of finished catalyst.

When vinyl acetate is prepared by the process of the present invention, a stream of gas, which contains ethylene, oxygen or air, acetic acid, a non-halogen containing copper compound and desirably an alkali metal acetate, is passed over the catalyst. The non-halogen containing copper compound is preferably somewhat water-soluble or acetic acid-soluble, e.g., at least about 0.3 g/l at 20° C., and may be, for example cupric acetate dihydrate which is preferred, cupric nitrate trihydrate or hexahydrate, cupric sulfate(anhydrous or pentahydrate), or cupric formate (anhydrous or pentahydrate) and the like. The composition of the gas stream can be varied within wide limits, taking into account explosive limits. For example, the molar ratio of ethylene to oxygen can be for example, about 80:20 to about 98:2, the molar ratio of acetic acid to ethylene can be for example, about 100:1 to about 1:100, the content of the copper compound can be such as to provide, for example, about 10 ppb (.parts per billion) to about 50 ppm (parts per million), preferably about 20 ppb to about 10 ppm of elemental copper relative to the acetic acid in the feed stream, and the content of alkali metal acetate, if used, can be for example, about 2–200 ppm, relative to the acetic acid employed. The copper compound and alkali metal acetate can conveniently be added to the feed stream by injecting into the stream a spray of an aqueous or acetic acid solution of both compounds or separate aqueous solutions of each compound, with the amounts of solution and levels of compound concentration sufficient to provide the desired levels of added copper and alkali metal acetate to make up for all or part of such components lost such components lost during the process. In addition to the foregoing active components of the feed stream, such stream also can contain inert gases, such as nitrogen, carbon dioxide and/or saturated hydrocarbons. Reaction temperatures which can be used are elevated temperatures, preferably those in the range of about 150°–220° C. The pressure employed can be a somewhat reduced pressure, normal pressure or elevated pressure, preferably a pressure of up to about 20 atmospheres gauge.

The presence of copper in the catalyst generally yields a higher initial vinyl acetate selectivity and productivity in the VA process due to a lower $CO_2$ selectivity than a catalyst limited to equivalent quantities of palladium and gold as catalytically active metals. However, because of the loss of copper due to its volatilization during the VA reaction, the fall of vinyl acetate selectivity and productivity due to a rise in $CO_2$ selectivity during the life of the catalyst tends to be greater than if the rate of copper loss were significantly reduced.

When the procedure described herein is followed except that 0.5 ppm of cupric acetate dihydrate, based on the weight of acetic acid, is added to the feed stream, the initial vinyl acetate productivity is comparable to that obtained when no copper compound is included in the feed stream, since the initial catalyst composition is the same. However, as the process continues well beyond its start-up point, the loss of copper is less when the feed stream contains cupric acetate, since the deposition of cupric acetate from the feed stream into the catalyst particles tends to make up for the loss of copper due to volatilization. This slower loss of copper from the catalyst during the reaction results in a higher vinyl acetate selectivity and productivity during the life of the catalyst and/or longer catalyst life, i.e., the period of reaction before the catalyst must be replaced or regenerated because of low vinyl acetate productivity.

It is to be understood that although the present invention describes the addition of a copper metal feed stream in combination with a Pd/Au/Cu catalyst, other feed streams will work with the corresponding metal catalyst combination. For example, a copper acetate feed stream will replenish copper lost due to volatilization of copper; likewise a potassium or cadmium acetate stream will replenish potassium or cadmium, respectively, lost in a Pd/Au/K or Pd/Au/Cd catalyst.

What is claimed is:

1. A process for the production of vinyl acetate by reaction of ethylene, oxygen and acetic acid as reactants comprising contacting said reactants and a non-halogen containing copper compound with a catalyst comprising a porous support on the porous surfaces of which is deposited catalytically effective amounts of metallic palladium, gold and copper.

2. The process of claim 1 wherein said copper compound is a soluble salt and is sprayed as an aqueous solute into the feed stream comprising said reactants.

3. The process of claim 1 wherein said copper compound is cupric acetate dihydrate.

4. The process of claim 1 wherein said copper compound is added in an amount to provide about 10 ppb to about 50 ppm of elemental copper based on the weight of acetic acid.

5. The process of claim 4 where said amount of copper compound provides about 20 ppb to about 10 ppm of elemental copper.

6. The process of claim 1 wherein said porous support is silica.

7. The process of claim 1 wherein said catalyst contains about 0.3 to about 5.0 grams of copper per liter of catalyst.

8. The process of claim 7 wherein said amount of copper is about 0.5 to about 3.0 grams per liter of catalyst.

9. The process of claim 7 wherein said catalyst contains about 1 to about 10 grams of palladium, and about 0.5 to about 10 grams of gold per liter of catalyst, with the amount of gold being from about 10 to about 125 weight percent based on the weight of palladium.

10. The process of claim 1 wherein said catalyst also contains a deposit of an alkali metal acetate.

11. The process of claim 10 wherein said alkali metal acetate is potassium acetate which is present in the catalyst in an amount of about 10 to about 70 grams/liter of catalyst.

12. The process of claim 1 wherein said catalyst is prepared by impregnating a porous support with an aqueous solution of water-soluble palladium and copper salts, fixing said palladium and copper as a water-insoluble compounds by reaction with an appropriate alkaline compound, subsequently impregnating the catalyst with a solution of a water-soluble gold salt, the amounts of elemental palladium, copper and gold in the impregnating solutions being equal to the predetermined amounts of metallic palladium, copper and gold desired in the catalyst, fixing on the catalyst the gold in the solution present in the latter impregnation by reacting the dissolved water-soluble salt in such solution with an appropriate alkaline compound to precipitate a water-insoluble gold compound, and reducing to free metallic form the water-insoluble compounds of palladium, copper and gold present in the catalyst.

13. The process of claim 12 wherein after the reduction of the total palladium, copper and gold on the catalyst, the catalyst is impregnated with a solution of an alkali metal acetate.

14. The process of claim 12 wherein in the preparation of said catalyst, said water-soluble copper salt is cupric nitrate trihydrate or cupric chloride dihydrate, said water-soluble palladium salt is palladium (II) chloride, sodium palladium (II) chloride, potassium palladium (II) chloride, palladium (II) nitrate or palladium (II) sulfate, said water-soluble gold salt is an alkali metal salt of auric (III) chloride or tetrachloroauric (III) acid, and said alkaline compound for fixing said palladium, copper and gold is sodium hydroxide.

15. The process of claim 10 wherein said alkali metal acetate is potassium acetate.

16. The process of claim 1 wherein said catalyst is prepared by impregnating the support with a solution of an amount of water-soluble palladium and copper salts containing all of the elemental palladium and copper desired on the finished catalyst and an amount of water-soluble gold salt containing only part of the elemental gold desired on the finished catalyst, fixing the palladium, copper and gold in the latter solution as water-insoluble compounds by rotating and/or tumbling the impregnated support while it is immersed in a solution of an appropriate alkaline compound, reducing the fixed palladium, copper and gold to their free metallic state, impregnating the catalyst with a solution of an amount of water soluble gold salt such that the total amount of elemental gold in the catalyst is equal to that desired in the finished catalyst, said latter solution also containing an amount of appropriate alkaline compound sufficient to fix the added gold as a water-insoluble compound, reducing the fixed added gold to its free metallic state.

17. The process of claim 16 wherein after the reduction of the total palladium, copper and gold on the catalyst, the catalyst is impregnated with a solution of an alkali metal acetate.

18. The process of claim 16 wherein in the preparation of said catalyst, said water-soluble copper salt is cupric nitrate trihydrate or cupric chloride dihydrate, said water-soluble palladium salt is palladium (II) chloride, sodium palladium (II) chloride, potassium palladium (II) chloride, palladium (II) nitrate or palladium (II) sulfate, said water-soluble gold salt is an alkali metal salt of auric (III) chloride or tetrachloroauric (III) acid, and said alkaline compound for fixing said palladium, copper and gold is sodium hydroxide.

19. The process of claim 17 wherein said alkali metal acetate is potassium acetate.

* * * * *